United States Patent
Lin et al.

(10) Patent No.: US 9,101,429 B2
(45) Date of Patent: Aug. 11, 2015

(54) METHOD AND APPARATUS FOR DELIVERING CEMENT PASTE INTO A BONE CAVITY

(76) Inventors: Jiin-Huey Chern Lin, Winnetka, IL (US); Chien-Ping Ju, Kansas, MO (US)

(*) Notice: Subject to any disclaimer, the term of this patent is extended or adjusted under 35 U.S.C. 154(b) by 20 days.

(21) Appl. No.: 13/410,362

(22) Filed: Mar. 2, 2012

(65) Prior Publication Data
US 2012/0277754 A1 Nov. 1, 2012

Related U.S. Application Data

(60) Provisional application No. 61/479,421, filed on Apr. 27, 2011.

(51) Int. Cl.
*A61B 17/88* (2006.01)
*B65B 3/12* (2006.01)
*B65B 3/00* (2006.01)

(52) U.S. Cl.
CPC ......... *A61B 17/8816* (2013.01); *A61B 17/8822* (2013.01); *A61B 17/8833* (2013.01); *B65B 3/003* (2013.01); *B65B 3/12* (2013.01)

(58) Field of Classification Search
CPC ...... A61B 17/8816; A61M 5/19; B65B 3/003
USPC .......................... 604/173, 191, 218, 230, 239; 606/92–94, 186; 222/137
See application file for complete search history.

(56) References Cited

U.S. PATENT DOCUMENTS

| | | | |
|---|---|---|---|
| 6,641,553 B1* | 11/2003 | Chee et al. | 604/68 |
| 7,736,049 B2* | 6/2010 | Keller | 366/155.1 |
| 8,579,986 B1* | 11/2013 | Freeman et al. | 623/23.63 |
| 2001/0053511 A1 | 12/2001 | Aoyagi et al. | |
| 2002/0049449 A1 | 4/2002 | Bhatnagar et al. | |
| 2002/0138038 A1* | 9/2002 | Ljungquist | 604/82 |
| 2004/0030320 A1 | 2/2004 | Chee et al. | |
| 2005/0228397 A1 | 10/2005 | Malandain et al. | |
| 2006/0259006 A1 | 11/2006 | McKay et al. | |
| 2008/0302821 A1* | 12/2008 | Crews | 222/145.5 |
| 2009/0032230 A1 | 2/2009 | Williams | |
| 2009/0163868 A1 | 6/2009 | Hoel et al. | |
| 2010/0010495 A1 | 1/2010 | Foster | |
| 2010/0056989 A1 | 3/2010 | McKay | |
| 2011/0009808 A1 | 1/2011 | AlGhamdi | |
| 2011/0068108 A1* | 3/2011 | Yeung | 220/500 |

FOREIGN PATENT DOCUMENTS

CN 101472539 A 7/2009

* cited by examiner

*Primary Examiner* — David Bates
(74) *Attorney, Agent, or Firm* — Bacon & Thomas, PLLC

(57) ABSTRACT

The present invention is related to a technique for simultaneously forming a plurality of paste filled tunnels. The plurality of paste filled tunnels are connected to a surgical tube directly or indirectly and emptied one after another, until a desired amount of the paste is injected into a bone cavity, organ or a tissue via the surgical tube. The paste may be a bone cement paste, a drug powder paste, viscous fluid or gel. The injected bone cement paste will set in the bone cavity to act as a medical implant.

11 Claims, 19 Drawing Sheets

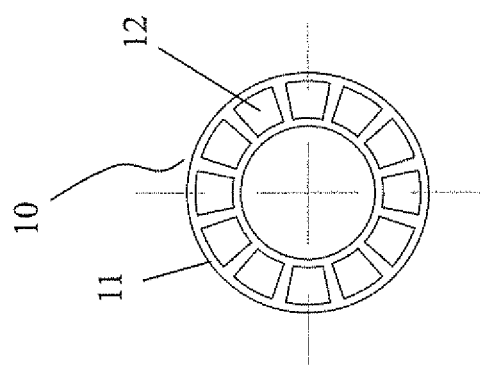
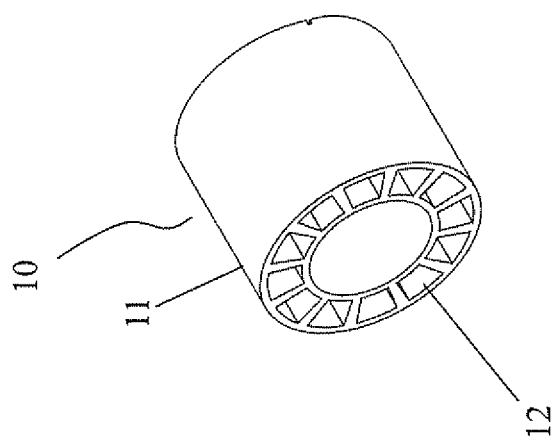
Fig. 9

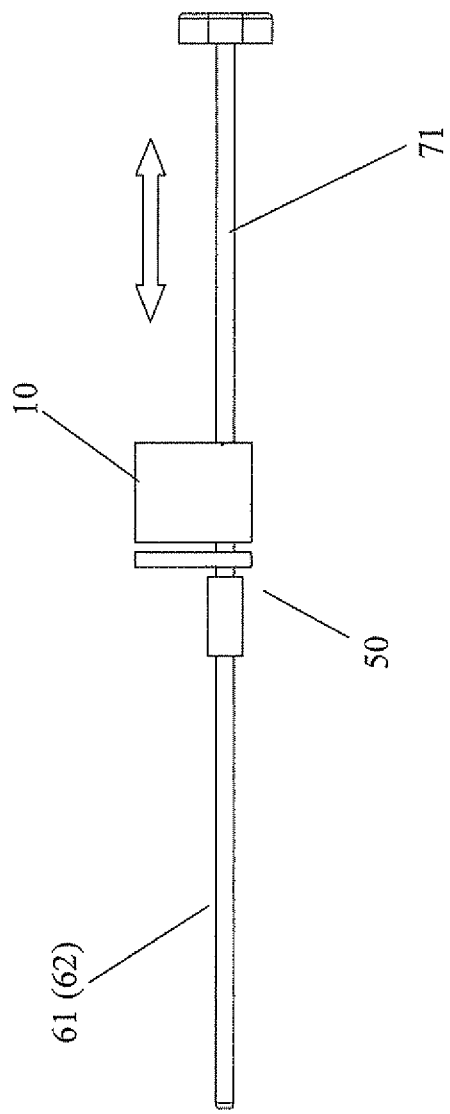

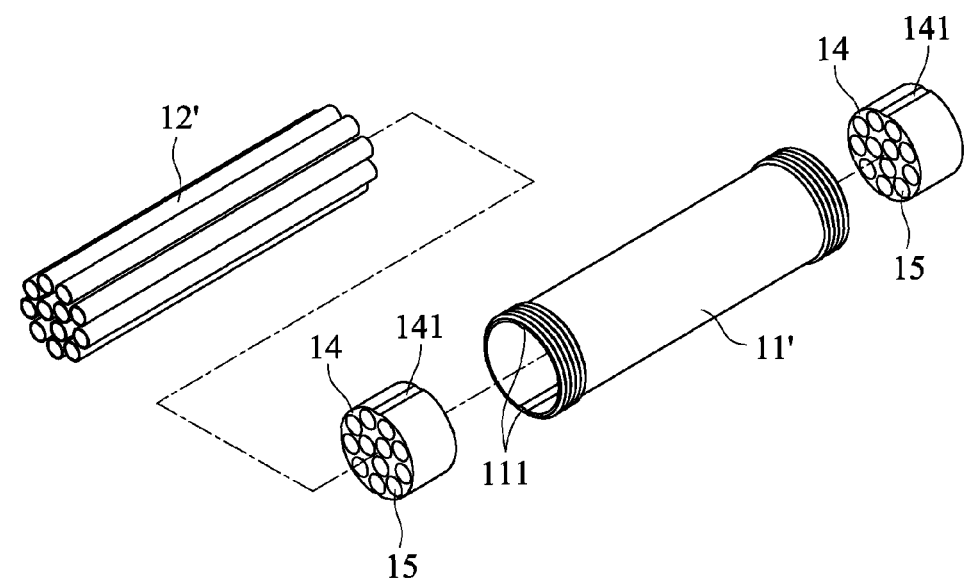
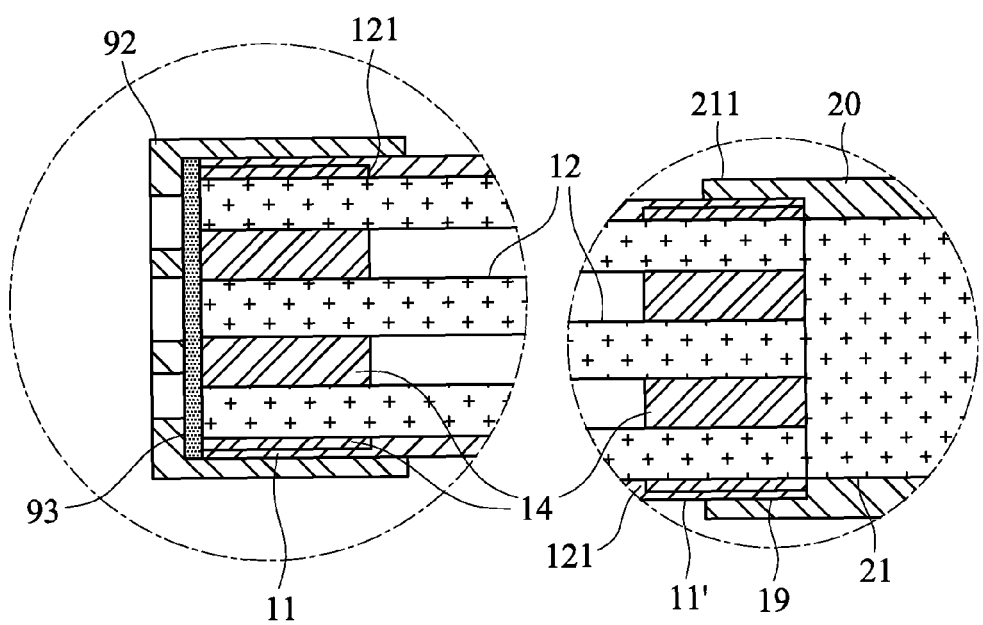
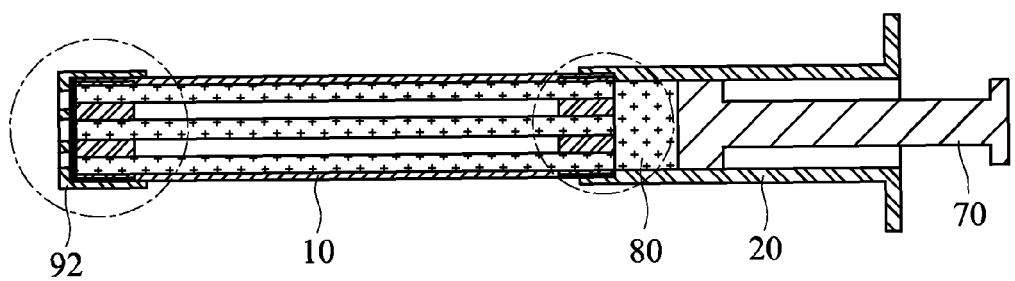
FIG. 15

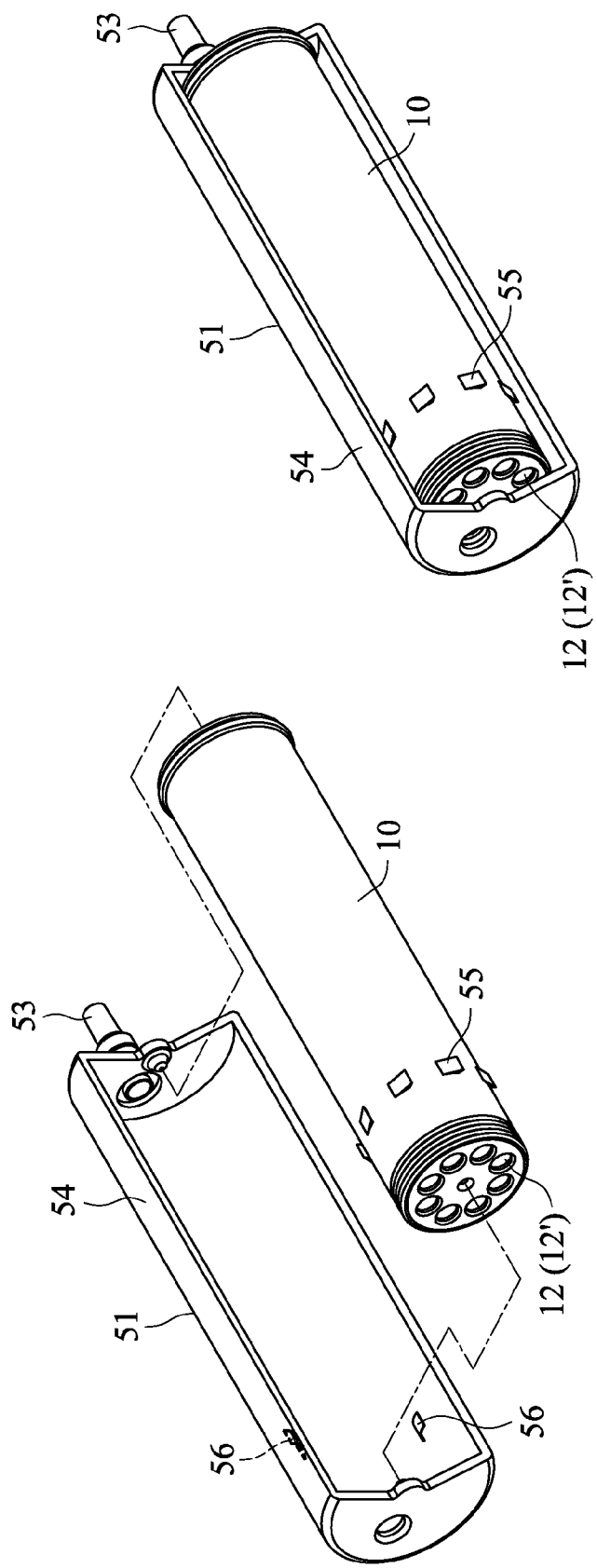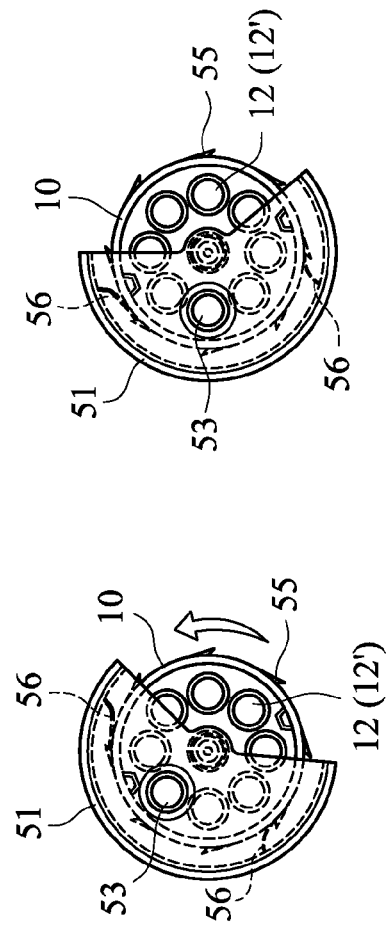
FIG. 19

METHOD AND APPARATUS FOR DELIVERING CEMENT PASTE INTO A BONE CAVITY

CROSS-REFERENCE TO RELATED APPLICATION

This patent application claims the benefit of U.S. Provisional Patent Application No. 61/479,421, filed Apr. 27, 2011.

FIELD OF THE INVENTION

The present invention is related to a technique for simultaneously forming a plurality of cement paste filled tunnels which are adapted to be connected to a surgical tube. The present invention is also related to a method for injecting a cement paste into a bone cavity, in which the cement paste will set to act as a medical implant.

BACKGROUND OF THE INVENTION

A common method for delivering a cement paste (or any other highly viscous paste) into a bone (or other tissue or organ of a diseased subject) cavity by a minimally invasive procedure is by pressing the paste into the cavity through a thin tube percutaneously inserted into the cavity. To fill in a bony cavity, PMMA and calcium-based cements are most commonly used. The cement paste is generally prepared by mixing a solid powder component with a liquid component (setting solution) at a proper ratio to form a paste. The mixed paste is set (hardened) and starts to gain its strength generally within minutes or tens of minutes, depending on the setting time of the formula being used.

To minimally invasively transport the cement paste into the cavity through a thin tube, conventionally, a syringe type device is used, wherein the mixed cement paste is stored in a container (reservoir) and pushed by a piston or a plunger through a small exit connected to a thin tube that has been percutaneously inserted into the bone cavity. Since the cross-sectional areas of the container and the exit are largely different (For example, the cross-sectional area of the container of a conventional 10 c.c. syringe is larger than that of its exit by about 60 times; and the cross-sectional area of the container of a conventional 20 c.c. syringe is larger than that of the exit by about 100 times), a large pressure is often implemented in order to push the cement out of the exit. However, larger pressures require more complicated designs in the delivery tool as well as higher costs. This problem becomes especially serious in delivering a highly viscous paste, such as PMMA and calcium-based cement. Although a more dilute paste prepared with a higher liquid/powder ratio may make the paste flow and be pushed through the small exit more easily, unfortunately, a dilute paste almost always leads to poor material properties. This is a big dilemma in this field. Theoretically, using a thin container (reservoir) with a diameter similar to that of the thin surgical tube (or connecting tube) may overcome the problem caused by the large difference in cross-sectional area between container and its exit. Practically, however, in so doing, an extremely long container is required. For example, to minimally invasively deliver a cement paste of 5 cc in volume through a container with an inner diameter of 1 mm would require a container of more than 6 meters in length; and to deliver a 10 cc cement paste through the same container would require a container longer than 12 meters! (A plunger of the same length is also required to drive the paste all the way to the container exit) This kind of length is practically impossible for any kind of surgery.

Furthermore, even if an extremely long, thin container is used, it would be practically impossible to transport the mixed cement paste into this thin container. When a regular syringe is used, the large cross-sectional difference-induced problem still remains in the transportation of the paste from the syringe into the thin container.

Another primary problem with the conventional syringe-type cement deliverer is that a larger pressure does not guarantee a more efficient delivery. In many cases (for example, for most calcium-based cements), the opposite is true. This is because that, before being fully hardened due to the reaction between powder and liquid, the cement paste is still a solid-liquid two phase material. Under pressure, the liquid phase tends to separate from the solid phase. Since the greatest pressure gradient occurs at the exit (thin neck) region, the liquid tends to flow out of the exit at a higher speed than the solid. Due to this solid-liquid separation effect, the cement paste coming out of the container at the early stage has a higher-than-desired liquid/powder ratio, causing properties of the cement to degrade. On the other hand, the cement remaining in the container, especially at the later stage, has a lower-than-desired liquid/powder ratio (because the lower-density liquid continues to be squeezed out of the container) and becomes difficult to flow out of the exit.

SUMMARY OF THE INVENTION

A primary object of the present invention is to provide a method and apparatus for injecting a cement paste into a bone cavity or like, in which the cement paste will set and act as an implant. More specifically, the present invention provides a technique for simultaneously forming a plurality of cement paste filled tunnels which are adapted to be connected to a surgical tube. According to one embodiment of the present invention the plurality of cement paste filled tunnels are connected to the surgical tube and emptied one-by-one, whereby a desired amount of cement paste is injected into the bone cavity.

Another object of the present invention is to provide a method and apparatus for injecting a drug powder paste, viscous fluid or gel into a site needing a treatment. The drug powder paste may be formed by a non-soluble drug powder dispersed in a liquid medium such as water, oil and any pharmaceutically acceptable liquid carrier. The viscous fluid for example may be an oil or a polymeric liquid with or without a drug dissolved or dispersed therein. The gel for example may be collagen, gelatin, or a bio-polymeric gel-like material with or without a drug dissolved or dispersed therein. The drug for example can be an anti-cancer agent, bone growth factor, neuron growth factor, or hormone. More specifically, the present invention provides a technique for simultaneously forming a plurality of tunnels filled with a drug powder paste, viscous fluid or gel, which are adapted to be connected to a surgical tube. According to one embodiment of the present invention the plurality of filled tunnels are connected to the surgical tube and emptied one-by-one, whereby a desired amount of the drug powder paste, viscous fluid or gel is injected into the site needing a treatment for example a vertebra, bone cavity, an organ such as brain and liver, or a tissue such as a joint, blood vessel, and muscle.

In order to accomplish the aforesaid objects of the present invention, a filling apparatus constructed according to the present invention comprises a plurality of parallel tunnels formed in a longitudinal body and in a longitudinal direction of said body; a filler reservoir having an exit end adapted to be in fluid communication with said plurality of parallel tunnels; and optionally a driver for driving a filler contained in said reservoir into said plurality of parallel tunnels via said exit end, wherein the cross-sectional area of said exit end is less than about 5 times of a total cross-sectional area of said plurality of parallel tunnels.

BRIEF DESCRIPTION OF THE DRAWINGS

FIG. 9 shows a donut-type receiver for cement paste to simultaneously flow into tunnels of the receiver according to one embodiment of the present invention.

FIG. 13 is a schematic side view showing that the donut-type receiver of the present invention is connected to a connecting tube (a surgical tube) with a gun device, wherein the cement pastes filled in the tunnels of donut-type receiver are automatically or semi-automatically delivered into the connecting tube (the surgical tube) one after another.

FIG. 15 shows a schematic perspective view of a modified tube-type receiver having two cylindrical tube holders, partially enlarged cross-sectional views thereof, and a cross-sectional view of the modified tube-type receiver together with a cement paste container and a piston constructed according to one embodiment of the present invention.

FIG. 19 shows a receiver for cement paste counterclockwise rotatably received in an outlet adapter with a ratchet mechanism for delivering the cement paste in the receiver according to one embodiment of the present invention.

DETAILED DESCRIPTION OF THE INVENTION

Figure 1:
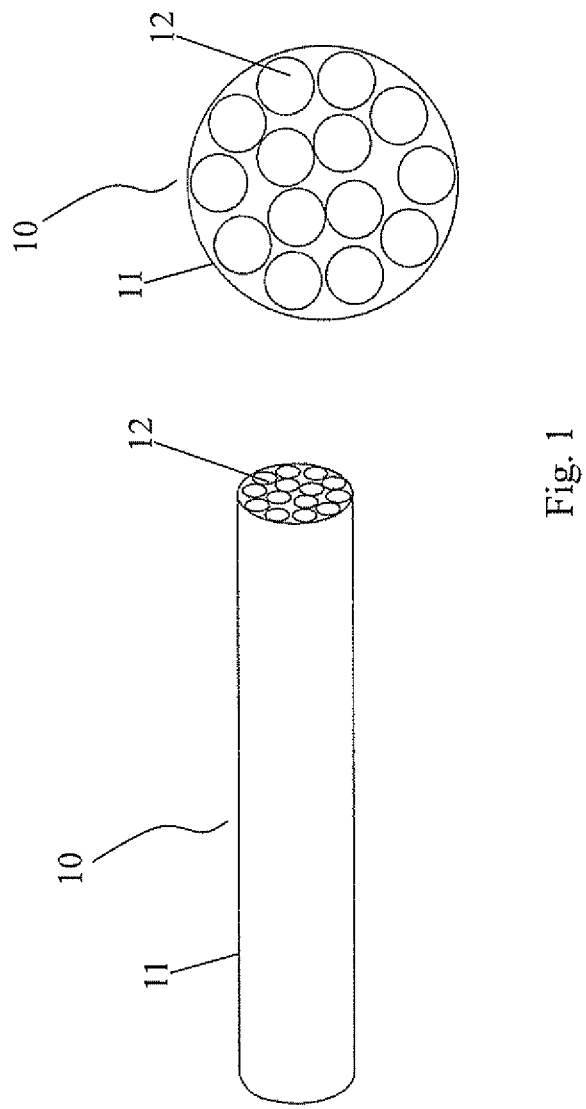
FIG. 1 shows a tunnel-type receiver for cement paste to simultaneously flow into tunnels of the receiver according to one embodiment of the present invention.

In the following, a general term "filler" is used to represent the cement paste, and the drug powder paste, viscous fluid or gel.

A filling apparatus constructed according to one embodiment of the present invention comprises a plurality of parallel tunnels formed in a longitudinal body and in a longitudinal direction of said body; and a filler reservoir having an exit end adapted to be in fluid communication with said plurality of parallel tunnels, wherein a cross-sectional area of said exit end is less than about 5 times of a total cross-sectional area of said plurality of parallel tunnels.

Preferably, said tunnels have an inner diameter of about 1 mm to about 10.0 mm and a length of about 10.0 mm to about 300 mm.

Preferably, the cross-sectional area of said exit end is less than about 3 times of a total cross-sectional area of said plurality of parallel tunnels, and more preferably about 1.5 to about 1.1 times of a total cross-sectional area of said plurality of parallel tunnels.

Preferably, said longitudinal body has a multi-tubular structure with said plurality of parallel tunnels being formed therein.

Preferably, the apparatus of the present invention further comprises a plurality of receiving tubes, wherein said longitudinal body is a hollow longitudinal body and said plurality of receiving tubes are received in said hollow longitudinal body such that said plurality of parallel tunnels are formed in said plurality of receiving tubes.

Preferably, the apparatus of the present invention further comprises two tube holders, wherein each of the two tube holders comprises a multi-tubular structure with a plurality of openings, and the two tube holders are connected to or one of them is connected to and the other one is adapted to be connected or both adapted to be connected to two ends of the hollow longitudinal body with said plurality of openings of the two tube holders being aligned with one another, such that said plurality of receiving tubes are mounted in said plurality of openings of the two tube holders respectively, and said plurality of parallel tunnels are formed in said plurality of receiving tubes.

Preferably, the hollow longitudinal body is a hollow cylindrical body, and the tube holder is a cylindrical tube holder, wherein each of the two ends of the hollow cylindrical body comprises an enlarged opening having a diameter equal to an outer diameter of said cylindrical tube holder; and the hollow cylindrical body comprises a regular opening between the two ends of the hollow cylindrical body; and a vertical wall (a step) at the interface of the enlarged opening and the regular opening, which is able to stop an insertion of the cylindrical tube holder into the regular opening of the hollow cylindrical body, wherein an alignment mechanism is provided on each of the ends of the hollow cylindrical body and on the cylindrical tube holder for said plurality of openings of the two cylindrical tube holders being able to be aligned with one another when the two cylindrical tube holders are connected to two ends of the hollow cylindrical body. More preferably, the alignment mechanism comprises an axial groove formed on a surrounding surface of the cylindrical tube holder, and an axial protrusion corresponding to the axial groove formed on an inner wall of the enlarged opening of the end of the hollow cylindrical body, or vice versa.

Alternatively, the apparatus of the present invention further comprises a plurality of receiving tubes, wherein said longitudinal body has a multi-tubular structure with a plurality of openings, and said plurality of receiving tubes are mounted in said plurality of openings respectively, so that said plurality of parallel tunnels are formed in said plurality of receiving tubes.

Preferably, said exit end of said reservoir has an opening having a diameter about equal to a diameter of said longitudinal body. More preferably, said exit end of said reservoir has a thinner wall portion having an inner diameter equal to an outer diameter of said longitudinal body, so that one end of said longitudinal body can be plugged into this thinner wall portion of the exit end of said reservoir.

Preferably, said longitudinal body has a donut like structure with an axial opening in said longitudinal direction of said body and said plurality of parallel tunnels being formed circumferentially around said axial opening, and said exit end of said reservoir has an annual opening corresponding to said donut like structure and in fluid communication with said plurality of parallel tunnels. Alternatively, said longitudinal body has a donut like structure and an axial dome protruding from a proximal end of the donut like structure, wherein said plurality of parallel tunnels are formed circumferentially and around said axial dome of said longitudinal body, and said exit end of said reservoir is leak-tightly connected to said proximal end of said donut like structure to form an annual opening around said axial dome and in fluid communication with said plurality of parallel tunnels. Said annual opening of said reservoir has a radial distance about equal to a radial thickness of said donut like structure.

Preferably, the apparatus of the present invention further comprises an air-penetrable film being provided to cover one end of said longitudinal body, so that air in said plurality of parallel tunnels is pushed out by said filler and said filler is retained in said plurality of parallel tunnels, when said filler contained in said reservoir is driven into said plurality of parallel tunnels by said driving means.

Preferably, said reservoir comprises a cylindrical container for receiving said filler, and said driving means is a dispensing plunger slidably received in said cylindrical container, so that the filler contained in said cylindrical container is able to be pushed by the plunger into said plurality of parallel tunnels via said exit end.

The present invention also discloses a method for simultaneously filling a filler in a plurality of parallel tunnels, said method comprising driving a filler contained in a reservoir into said plurality of parallel tunnels via an exit end of said reservoir, wherein said exit end is in fluid communication with said plurality of parallel tunnels, and the cross-sectional area of said exit end is less than about 5 times of a total cross-sectional area of said plurality of parallel tunnels.

Preferably, said plurality of parallel tunnels in the aforesaid method of the present invention are the plurality of parallel tunnels of the aforesaid filling apparatus of the present invention.

Preferably, said reservoir comprises a cylindrical container for receiving said filler, and a dispensing plunger slidably received in said cylindrical container is pressed to push the filler contained in said cylindrical container into said plurality of parallel tunnels via said exit end. Preferably, said filler is cement paste.

The present invention further provides a method of injecting filler into a site comprising the following steps: a) providing a filler simultaneously filled in a plurality of parallel tunnels; b) introducing the filler in said tunnel into a tube with one end thereof in said site and another end thereof in fluid communication with said tunnel; c) removing said tunnel from said tube after said filler in said tunnel being at least partially introduced into said tube in step b); and d) optionally repeating step b) and step c) by using another tunnel filled with said filler in step a) until a desired amount of filler is injected into said site.

Preferably, said providing a filler simultaneously filled in a plurality of parallel tunnels in step a) is accomplished by the aforesaid method for simultaneously filling a filler in a plurality of parallel tunnels of the present invention.

Preferably, step b) comprises connecting one end of said tunnel to said another end of said tube, so that said one end of said tunnel is in fluid communication with said another end of said tube; and pushing said filler in said tunnel from another end thereof. More preferably, said pushing comprises inserting a plunger into said another end of said tunnel and pressing said plunger to move from said another end of said tunnel to said one end of said tunnel.

Preferably, step b) comprises connecting said tunnel to said tube by receiving said another end of said tube in one end of said tunnel; and pressing another end of said tunnel with the filler entrapped therein to move from said another end of said tube toward said one end of said tube, wherein an air-penetrable film is provided to cover said another ends of said plurality of parallel tunnels, so that the filler entrapped in each of said plurality of parallel tunnels is delivered from said tunnel into said tube.

Preferably, said plurality of parallel tunnels are formed circumferentially in a longitudianl body, and step c) comprises revolving said longitudianl body after said filler in said tunnel being at least partially introduced into said tube in step b), so that another tunnel filled with said filler adjacent to the at least partially empty tunnel is aligned to said another end of said tube.

Preferably, said site is a bone cavity, and said filler is cement paste.

In one of the preferred embodiments of the present invention a system for filling a cavity (preferably, but not limited to, a bone cavity) is disclosed, which comprises:
(a) a powder component;
(b) a liquid component;
(c) a mixing mechanism for mixing said powder and said liquid;
(d) a container (reservoir) for collecting the mixed cement paste;
(e) a receiver comprising multiple dispensing units, e.g. tunnels, tubes or partitioning openings, wherein an exit end of the container is adapted to be attached to a receiver, and a piston inserted from an entrance end of the container can push the mixed cement paste into the receiver, that is the mixed cement paste pushed by the piston can simultaneously flow into each dispensing unit; and
(f) optionally, a surgical tube to be inserted into a cavity.

Advantages over conventional syringe devices:
(i) The difference between the cross-sectional area of the container (reservoir) and the total cross-sectional area of the exit is dramatically reduced, thereby greatly reducing the pressure required to push the cement paste out of the exit.
(ii) A more viscous cement paste can be delivered, resulting in better performance of the hardened cement paste.
(iii) The undesired liquid-powder separation phenomenon is largely eliminated, resulting in a more uniform distribution in liquid-powder ratio and cement paste properties throughout the entire delivery procedure.
(iv) The elimination of liquid-powder separation guarantees a better cement paste delivery efficiency (percentage of the cement paste that can be uniformly transported through the thin tube).
(v) Delivery of a highly viscous cement paste through a thinner (than conventionally used) tube becomes possible.
(vi) The simultaneous flow of the cement paste into multiple dispensing units largely reduces the delivery time, thereby increasing the reliability (decreasing the risks) of the procedure.

In the following description, for purposes of explanation, specific nomenclature is set forth to provide a thorough understanding of embodiments of the present invention. It will be apparent to one skilled in the art that specific details in the description may not be required to practice the embodiments of the present invention.

Powder Component

The powder component, that is able to form a cement paste while mixing with a liquid component (a setting solution), may be prepared from any biocompatible material, such as a calcium-based material (calcium phosphate, calcium sulfate, etc.), polymer-based material (PMMA, biodegradable polymer, etc.), bioactive glass, or drug/growth factor-carrying microbeads.

Liquid Component

The liquid component can be any setting solution that is able to form a cement paste while mixing with the powder component. The liquid can be a water-based, oil-based or polymer-based liquid.

Mixing Mechanism

The mixing mechanism can be any commonly known manual mixing or automatic mixing mechanism. The mixing can be carried out through moving blades, pressurized air stirring, ball-mill mixing, grinding mixing, or container shaking/rotating. The automatic mixing can be activated electrically or by vacuum/pressure activation.

Container (Reservoir)

The container can be of any shape, depending on application and fabrication conveniences. The container, which is preferably, but not limited to, cylindrical-shaped (similar to a regular syringe, except the exit end with a special design), is for collecting the mixed cement paste. An exit end of the container is attached to a receiver. A piston can be inserted from an entrance (paste-receiving) end of the container, pushing the cement paste into the receiver by thumb or any common device. For the conveniences of most clinical applications, typically, the container has an inner diameter from about 10 mm to about 50 mm and a length from about 50 mm to about 150 mm.

Receiver

Three different types of receivers are disclosed: (1) "tunnel-type" receiver; (2) "tube-type" receiver; and (3) "donut-type" receiver. However, others can also be designed with the same principle and spirit.

Tunnel-Type Receiver

As shown in FIG. 1, this type of receiver 10 has a cylindrical longitudinal body 11 and a plurality of parallel tunnels 12 formed in the longitudinal body. The longitudinal body 11 has a multi-tubular structure with the plurality of parallel tunnels 12 being so compact such that as many parallel tunnels 12 as possible are formed. The unique design of the tunnel-type receiver allows the mixed cement paste pushed by the piston from the container to simultaneously flow into each dispensing tunnel. The cement pastes filled in the tunnels are readily to be injected into a bone cavity one at a time via a surgical tube which has an outer or inner diameter about equal to the inner diameter of the tunnel. This design dramatically reduces the cement paste delivery time, which is critical due to the limited working time of the cement paste, especially for minimally invasive procedures that require a very thin tube to be percutaneously inserted into a bone cavity.

Furthermore, this inventive design dramatically reduces the difference between the cross-sectional area of the container (reservoir) and the total cross-sectional area of all the tunnels, thereby greatly reducing the pressure required to push the cement paste out of the exit of the container. For a more satisfactory result, the cross-sectional area of the container (the exit end) is preferably less than 3 times of the total cross-sectional area of all the tunnels; more preferably less than 2 times of the total cross-sectional area of all the tunnels. As a comparison, the cross-sectional area of the container of a conventional 10 c.c. syringe is larger than that of its exit by about 60 times; and the cross-sectional area of the container of a conventional 20 c.c. syringe is larger than that of its exit by about 100 times. The difference between the cross-sectional area of the container (reservoir) and the cross-sectional area of all the tunnels in the tunnel-type receiver of the present invention is dramatically reduced, which in turn greatly increases the cement paste delivery efficiency and reduces the solid-liquid separation effect that largely hinders the delivery of the cement paste, as mentioned above.

The tunnel-type receiver is preferably, but not limited to, cylindrical-shaped, and preferably has a similar shape as the container. The receiver has a diameter from about 10 mm to about 50 mm and a length from about 50 mm to about 150 mm. The tunnels running through the receiver and parallel to the longitudinal axis of the cylindrical body have a substantially same diameter. Each individual tunnel has a diameter from about 1 mm to about 3 mm, depending on the application. The tunnels are as "close-packed" as possible, so that the difference in the cross-sectional area of the container and the total cross-sectional area of all the dispensing tunnels may be minimized.

Figure 2:
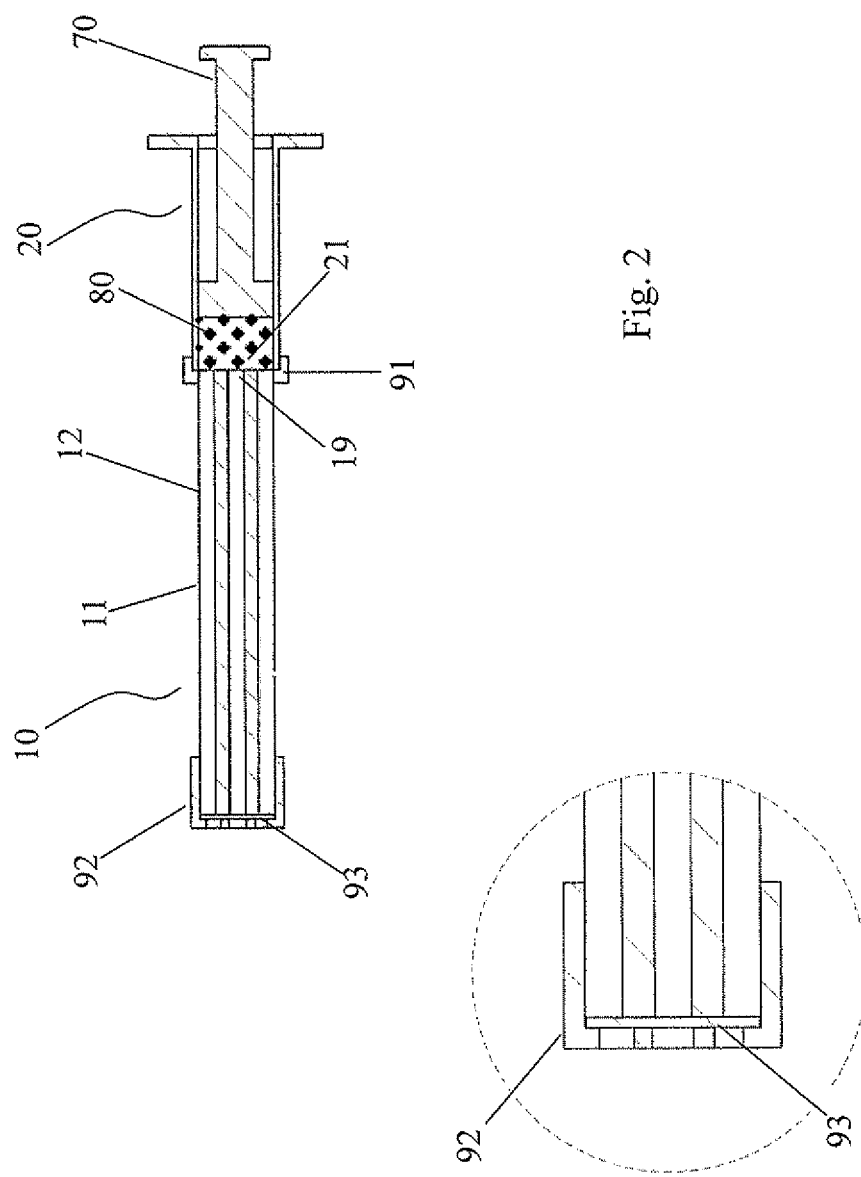
FIG. 2 shows a cross-section view of the tunnel-type receiver shown in FIG. 1, a cement paste container and a piston constructed according to the present invention, and a partially enlarged cross-sectional view thereof, wherein a cement paste is pushed from the piston to simultaneously flow into tunnels of the receiver.

As shown in FIG. 2, a connector 91 leak-tightly connects the exit end 21 of the container 20 to a proximal end 19 of the tunnel-type receiver 10, so that the exit end 21 is in fluid communication with the plurality of parallel tunnels 12. Depending on how the two components are fastened, the following three options are possible: (1) the inner diameter of the exit end 21 is equal to the outer diameter of the longitudinal body 11; (2) the outer diameter of the exit end 21 is equal to the outer diameter of the longitudinal body 11; or (3) the outer diameter of the exit end 21 is slightly smaller than the outer diameter of the longitudinal body 21. A perforated cap 92 is mounted to a distal end of the receiver 10 to fasten an air-penetrable film 93 between the perforated cap 92 and the receiver 10, so that air in said plurality of parallel tunnels 12 is pushed out by the cement paste 80 and the cement paste 80 is retained by the air-penetrable film 93 in said plurality of parallel tunnels 12, when said cement paste 80 contained in said container 20 is driven into said plurality of parallel tunnels 12 by the piston 70. Optionally, the tunnel may be slightly enlarged at the proximal end 19 (diameter is increased at the end of the tunnel) to more easily allow the cement paste to flow into the tunnel and be pushed into a surgical tube (or connecting tube). The receiver can be made from any medical-grade metallic or polymeric material, for example, stainless steel, PU, PP, PE, Teflon®, etc. The tunnels may be prepared from any commonly known method, e.g., mechanical drilling, laser drilling, extrusion, injection molding, etc.

Figure 3:
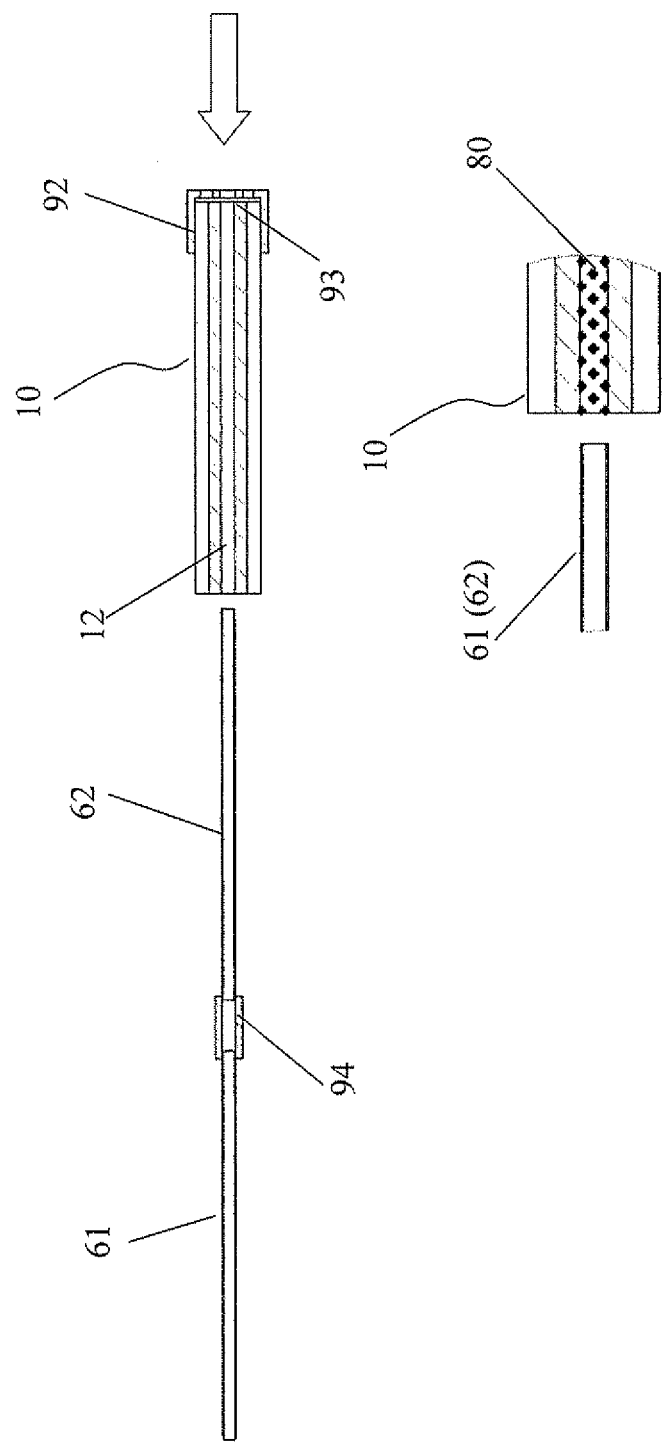
FIG. 3 shows a cross-section view of the tunnel-type receiver filled with cement paste, a connecting tube and a surgical tube constructed according to the present invention, and a partially enlarged cross-sectional view thereof, wherein a cement paste is transferred from the tunnel into the connecting tube and surgical tube.

As shown in FIG. 3, a connector 94 is used to leak-tightly connect the surgical tube 61 and the connecting tube 62, when one end of the surgical tube 61 is percutaneously inserted into a bone cavity and the remaining portion thereof is not long enough for directly delivering the cement paste from the tunnels without a plunger. The tunnel 12 has an inner diameter slightly greater than the outer diameter of the surgical tube 61 or the connecting tube 62, and is coupled to the other end of the surgical tube 61 (or connecting tube 62). The receiver 10 is pushed toward the surgical tube 61 or the connecting tube 62, which slides in the cement paste filled tunnel 12, and most of the cement paste 80 is now transferred from the tunnel 12 into the surgical tube 61 or the connecting tube 62 with the pushed end closed either by the cap 92 and the film 93 or by a finger. The cement pastes 80 filled in the tunnels 12 thus can be directly pushed into the surgical tube 61 (or connecting tube 62), one at a time, until a desired amount of cement paste is delivered into the bone cavity via the surgical tube and optionally the connecting tube.

Figure 4:
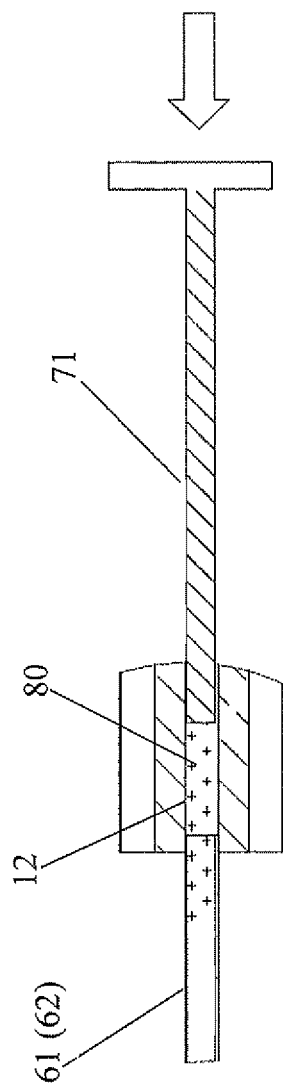
FIG. 4 shows a cross-section view of the tunnel-type receiver filled with cement paste, and a connecting tube (a surgical tube) constructed according to the present invention, wherein a cement paste is delivered from the tunnel into the connecting tube (the surgical tube) with a plunger.

Alternatively, the cement pastes 80 filled in the tunnels 12 may be pushed into the surgical tube 61 (or connecting tube 62), one at a time, by a plunger 71, as shown in FIG. 4.

Tube-Type Receiver

Figure 5:
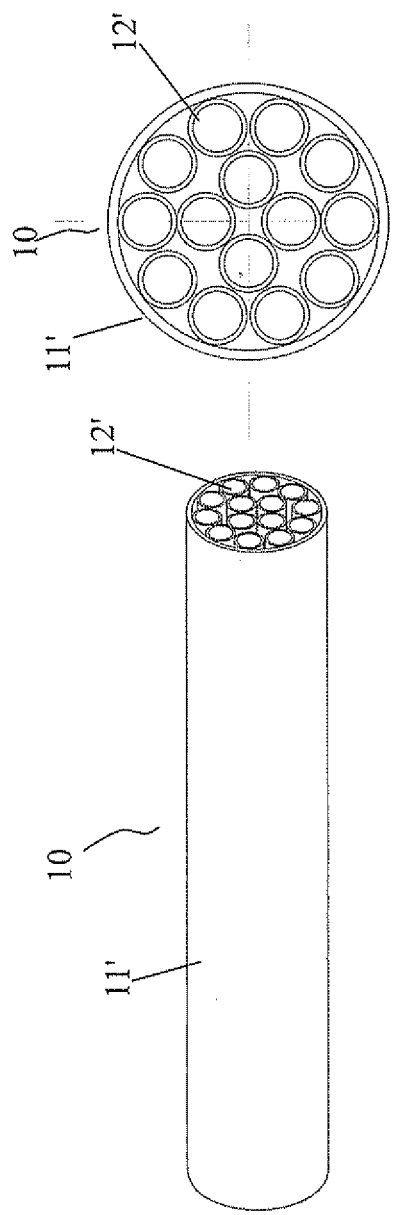
FIG. 5 shows a tube-type receiver for cement paste to simultaneously flow into receiving tubes of the receiver according to one embodiment of the present invention.
Figure 6:
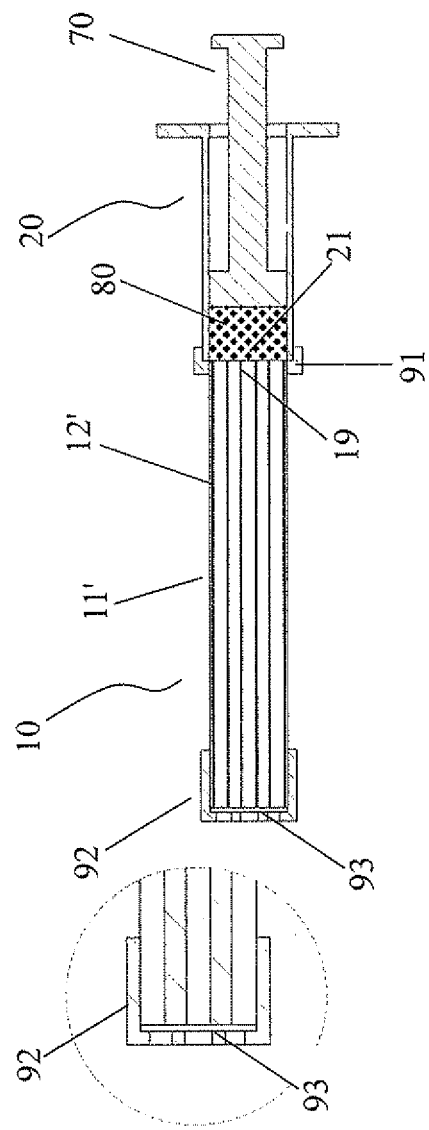
FIG. 6 shows a cross-section view of the tube-type receiver shown in FIG. 5, a cement paste container and a piston constructed according to the present invention, and a partially enlarged cross-sectional view thereof, wherein a cement paste is pushed from the piston to simultaneously flow into tubes of the receiver.

As shown in FIGS. 5 and 6, the receiver 10 may be a hollow body 11' (similar to a pipe), preferably has a cylindrical shape, similar to the tunnel-type receiver. The hollow cylindrical body 11' encloses multiple receiving tubes 12' running parallel to the longitudinal axis of the hollow cylindrical body 11', wherein the mixed cement paste 80 pushed from the piston 70 can simultaneously flow into each receiving tube 12'. The receiving tubes 12' are preferably close-packed in the hollow cylindrical body 11', so that the difference in the cross-sectional area of the container 20 and the total cross-sectional area of all the receiving tubes may be minimized. Similar to the tunnel-type receiver a connector 91 leak-tightly connects the exit end 21 of the container 20 to a proximal end 19 of the tube-type receiver 10, so that the exit end 21 is in fluid communication with the plurality of receiving tubes 12'. A perforated cap 92 is mounted to a distal end of the receiver 10 to fasten an air-penetrable film 93 between the perforated cap 92 and the receiver 10 to avoid air accumulation in the receiving tubes 12' and to avoid the cement paste leaking from the receiver 10, when the cement paste 80 is pushed by the piston 70 to simultaneously flow into each receiving tube 12'. Alternatively, the hollow cylindrical body 11' may be replaced by a cylindrical body having a multi-tubular structure similar to the cylindrical longitudinal body 11 shown in FIG. 1, and the receiving tubes 12' are slidably received in the plurality openings of the multi-tubular structure so that the cement paste 80 can be pushed by the piston 70 to simultaneously flow into each receiving tube 12'. It is apparent that the tunnels 12 in the tunnel-type receiver as shown in FIG. 1 are now the longitudinal holes in the receiving tubes 12 as shown in FIG. 5.

The tube-type receiver is preferably, but not limited to, cylindrical-shaped, and preferably has a similar shape as the container. The hollow cylindrical body 11' has a diameter from about 10 mm to about 50 mm and a length from about 50 mm to about 150 mm. Each individual receiving tube 12' has an inner diameter from about 1 mm to about 3 mm, depending on the application.

The tube-type receiver and the tunnel type receiver are similar in construction and function; however, each individual receiving tube 12' in the tube-type receiver after simultaneously filled with the cement paste can be taken out from the hollow cylindrical body 11' and applied separately. Accordingly, more than one bone cavities can be simultaneously injected with the cement paste, when the tube-type receiver is used.

Figure 7:
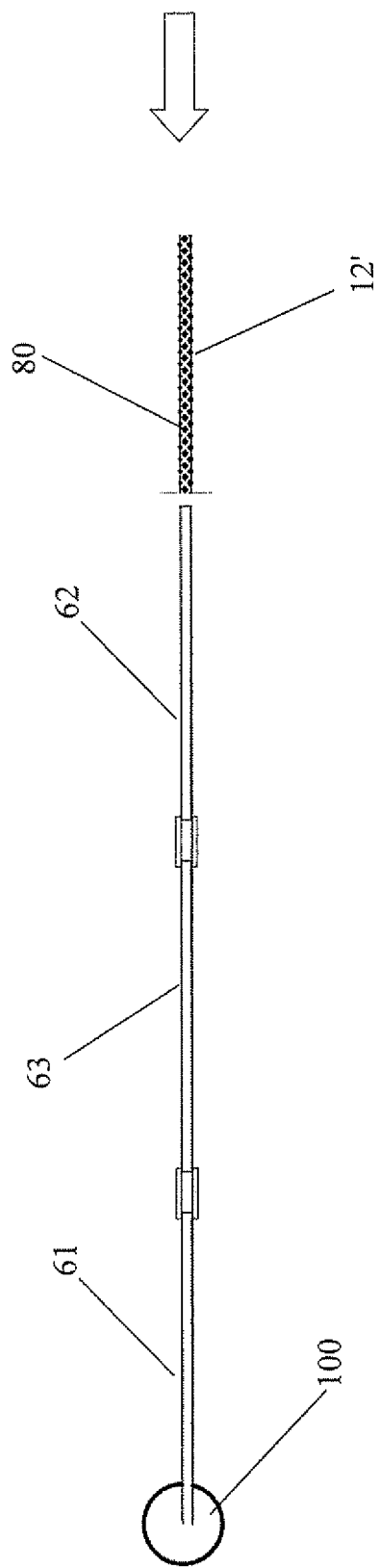
FIG. 7 shows a cross-section view of the receiving tube filled with cement paste, a connecting tube, an extension tube, and a surgical tube constructed according to one embodiment the present invention, wherein a cement paste is transferred from the receiving tube into the connecting tube, extension tube and surgical tube.

The individual receiving tube 12' filled with cement paste can be coupled to a surgical tube 61 directly, or via a connecting tube, or via an extension tube 63 and a connecting tube 62 as shown in FIG. 7, wherein the inner diameter of the receiving tube 12' is slightly greater than those of the surgical tube 61, connecting tube 62, and extension tube 63. The cement paste in the receiving tube 12' is then transferred into the surgical tube 61 directly or indirectly without a plunger as described in the aforesaid tunnel-type receiver case (FIG. 3). The cement pastes 80 filled in the receiving tubes 12' thus are eventually injected into a bone cavity 100, one at a time, until a desired amount of cement paste is injected.

Figure 8:
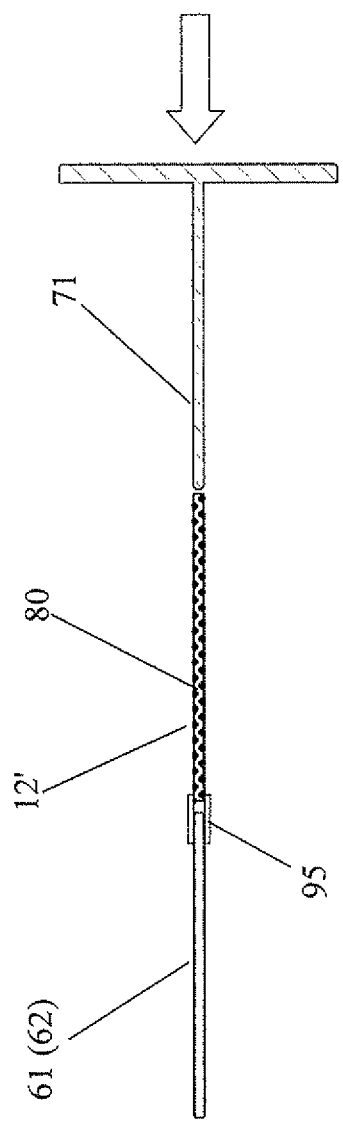
FIG. 8 shows a cross-section view of the receiving tube filled with cement paste, and a connecting tube (a surgical tube) constructed according to one embodiment the present invention, wherein a cement paste is delivered from the receiving tube into the connecting tube (the surgical tube) with a plunger.

Alternatively, the cement pastes 80 filled in the receiving tubes 12' may be pushed into the surgical tube 61 (or connecting tube 62), one at a time, by a plunger 71, as shown in FIG. 8, wherein a connector 95 is used to leak-tightly connect the receiving tube 12' and the surgical tube 61 (or connecting tube 62). In this case, the receiving tube 12' can have an inner diameter and outer diameter the same as those of the surgical tube 61 and connecting tube 62. The tube-type receiver can be made from any medical-grade metallic or polymeric material, for example, stainless steel, PU, PP, PE, Teflon®, etc. The tubes may be prepared from any commonly known method, e.g., extrusion, injection molding, etc.

Donut-Type Receiver

Figure 10:
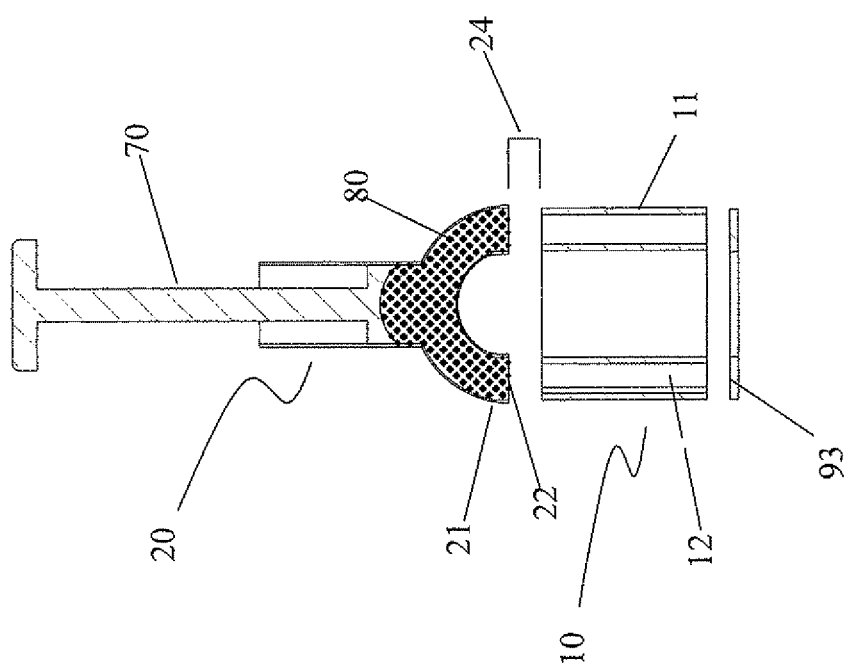
FIG. 10 shows a cross-section view of the donut-type receiver shown in FIG. 9, a cement paste container and a piston constructed according to the present invention, wherein a cement paste is pushed from the piston to simultaneously flow into tunnels of the receiver.

Alternatively, the receiver may have a donut like structure. As shown in FIG. 9, the donut-type receiver 10 has a longitudinal cylindrical body 11 with an axial opening and a plurality of parallel tunnels 12 being formed circumferentially around said axial opening. The enlarged exit end 21 of the container 20, as shown in FIG. 10, has an annual opening 22 corresponding to said donut like structure. The receiver diameter is typically larger than the diameter of the container 20. The annual opening 22 of the container 20 has outer and inner diameters substantially the same as those of the receiver 10, so that the container 20 and the receiver 10 can be easily connected and disconnected by a quick connector 24. The mixed paste cement 80 in the container 20 can be pushed by the piston 70 to simultaneously flow into each tunnel 12 of the receiver 10, when they are connected. An air-penetrable film 93 is used to cover tunnels 12 from the lower end of the receiver 10, so that air will not be trapped in the tunnels 12, and that no excess cement paste is leaked from the tunnels 12. To more efficiently transport the mixed cement paste 80 from the container 20 into the donut-shaped receiver 10, the piston 70 slidably received in the container 20 preferably has a substantially concave down dome shape.

The donut-type receiver 10 has an outer diameter from about 20 mm to about 100 mm, an inner diameter from about 10 mm to about 90 mm, and a length from about 10 mm to about 100 mm. Each tunnel 12 has a diameter from about 1 mm to about 3 mm, depending on the application. The tunnels 12 in the longitudinal cylindrical body 11 are as "close-packed" as possible, so that the difference in the cross-sectional area of the annual opening 22 of the container 20 and the total cross-section area of all the tunnels 12 of the receiver 10 may be minimized. For a more satisfactory result, the cross-sectional area of the annual opening 22 of the container 20 is preferably less than 3 times, and more preferably less than 2 times of the total cross-sectional area of all the tunnels 12 of the receiver 10.

Figure 12:
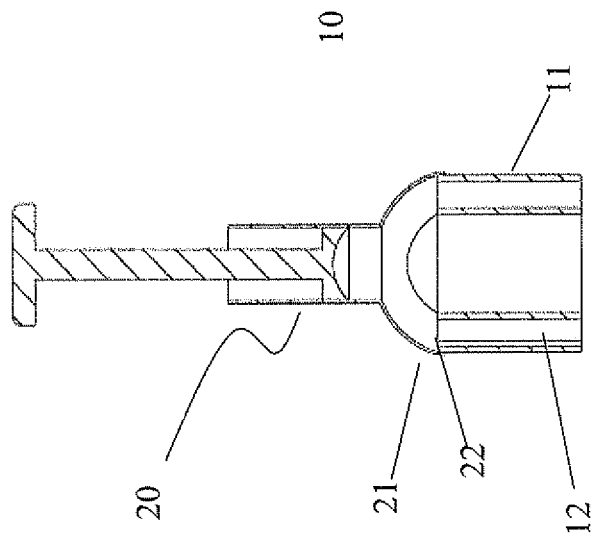
FIG. 12 shows a cross-section view of the modified donut-type receiver shown in FIG. 11, a cement paste container and a piston constructed according to the present invention, wherein a cement paste is pushed from the piston to simultaneously flow into tunnels of the receiver.
Figure 11:
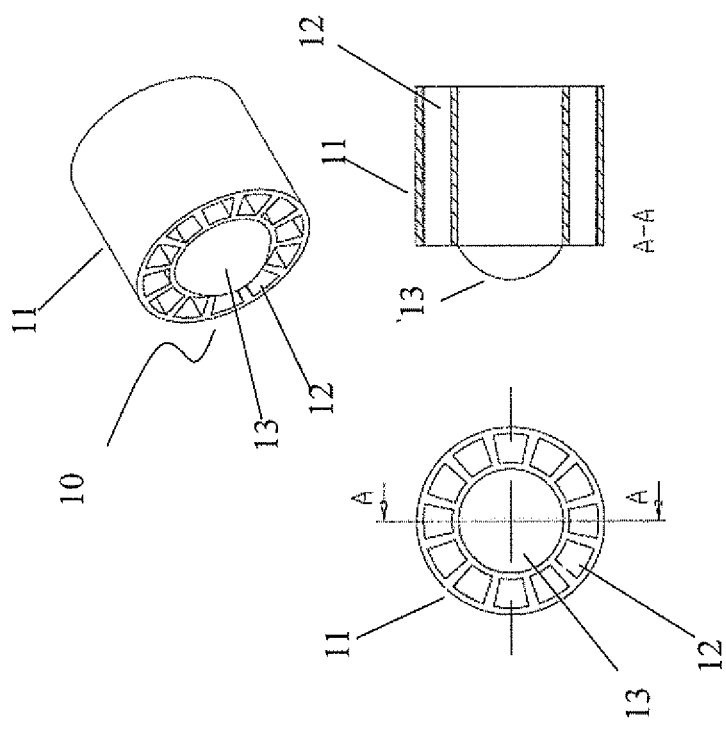
FIG. 11 shows a modified donut-type receiver for cement paste to simultaneously flow into tunnels of the receiver according to one embodiment of the present invention.

Alternatively, the longitudinal body 11 of the donut-type receiver 10 has an axial dome 13 protruding from a proximal end of the donut like structure, wherein the plurality of parallel tunnels 12 are formed circumferentially and around said axial dome 13 of said longitudinal body 11, and the enlarged exit end 21 of the container 20 is leak-tightly connected to said proximal end of said donut like structure to form an annular opening 22 around said axial dome 13 and in fluid communication with said plurality of parallel tunnels 12, as shown in FIGS. 11 and 12.

A unique advantage for the donut-receiver design is that the receiver 10 (cartridge 10) can be easily and quickly attached to a "gun" device 50 and the cement paste in each tunnel of the cartridge can be injected automatically or semi-automatically by the gun device as shown in FIG. 13. In this gun-type deliverer design, a plunger 71 is incorporated to push the cement paste out of each tunnel. The plunger has a diameter slightly smaller than the diameter of the tunnel, so that the plunger may go in and out the tunnel smoothly. The plunger may be inserted partly or all the way into each tunnel of the cartridge. The linear movement of the plunger may be driven by any common mechanism.

The gun device 50 further comprises a mechanism to drive the cartridge 10 to rotate about the longitudinal axis of the cartridge, so that, after each stroke, the cartridge 10 rotates to a new position where the followed-up tunnel is in alignment with the plunger 71 and the surgical tube 61 (or connecting tube 62). The rotation of the cartridge can be driven by any common mechanism. This injection/rotation movement is repeated and the cement paste is injected out of each tunnel, one after another, until a desired amount of paste is delivered out of the cartridge.

The donut-type receiver can be made from any medical-grade metallic or polymeric material, for example, stainless steel, Teflon®, PP, PE, PU, etc. The multiple tunnels of the cartridge may be prepared from any commonly known method, e.g., machining, mechanical drilling, laser drilling, extrusion, and injection molding, etc.

According to the present invention, after all tunnels (for the tunnel-type receiver and donut-type receiver), and receiving tubes (for the tube-type receiver) are filled with paste, the receiver is disconnected from the container. The paste-exposing end (the end attached to the container exit) is then used as the front-end (the end approaching the surgical tube or the connecting tube, depending on the application), while delivering the cement paste into the surgical tube or connecting tube.

The surgical tube suitable for use in the present invention is a tube to be inserted into the cavity to facilitate delivery of the cement paste. For minimally invasive procedures, the surgical tube is preferably a small-diameter, thin-walled tube that may be percutaneously inserted into a bone cavity with minimal wounds. The surgical tube has an inner diameter from about 1 mm to about 3 mm, and a length from about 50 mm to about 250 mm, depending on the application. The surgical tube is preferably made from a high strength, medical-grade metal such as stainless steel, and titanium alloys, etc. The surgical tube may be manufactured by any common methods. Preferably a thin rod with a sharp head to facilitate drilling or hammering is enclosed in the surgical tube. After an opening is created by the drilling or hammering, the thin rod is retrieved and the surgical tube is left in the cavity. If the surgical tube is sufficiently long, the cement paste filled in each tunnel or tube may be directly transported into the surgical tube.

The connecting tube (preferably made from, but not limited to, a bendable, polymeric material, for example, PU, PP, PE, and Teflon®, etc.) used in the present invention is incorporated to connect the tunnel or receiving tube filled with cement paste and the surgical tube. In this case the paste in each tunnel or receiving tube is transferred into the connecting tube and later pushed into the surgical tube by the followed-up cement paste.

The extension tube used in the present invention (preferably made from a bendable, polymeric material, for example, PU, PP, PE and Teflon®, etc.) is further incorporated to connect the connecting tube and the surgical tube. The use of this extension tube is to keep surgeon's hands farther from the x-ray-guided surgical site as well as for the surgeon to more easily handle the apparatus during the operation. In this case the paste in each tunnel (or receiving tube) is first transferred into the connecting tube, followed by the extension tube, and eventually the surgical tube, one tunnel (or receiving tube) after another, the cement paste is delivered all the way into the cavity through the surgical tube by the followed-up cement paste.

The surgical tube, connecting tube and extension tube have substantially the same internal diameter. Preferably, a plunger with a diameter slightly smaller than the internal diameter of the surgical tube, connecting tube and extension tube is provided, that is able to clear/push the cement paste remaining in any parts of the tubes into the cavity.

Figure 14:
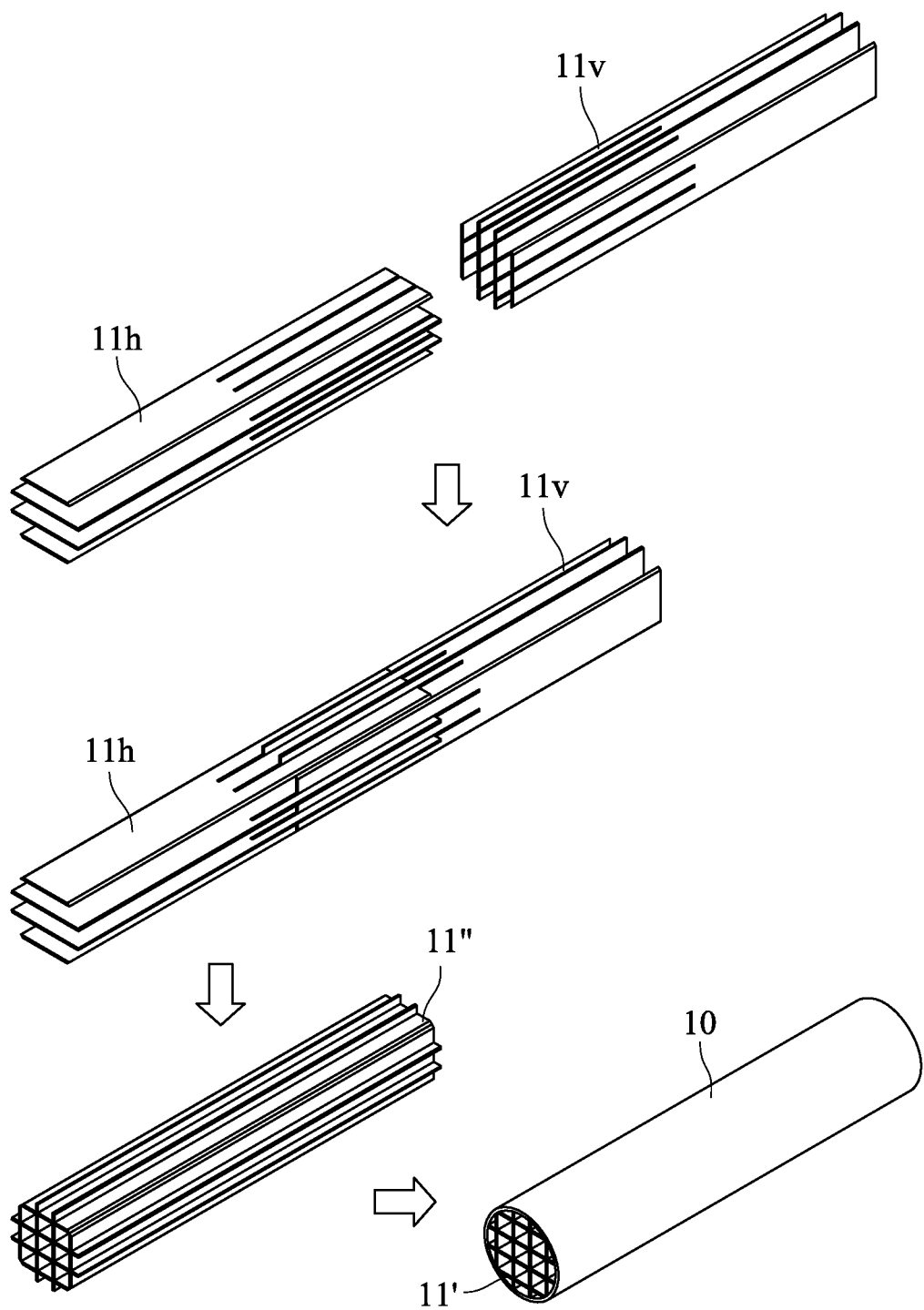
FIG. 14 is a schematic perspective view showing a modified tunnel-type receiver for cement paste according to one embodiment of the present invention.

A modified tunnel-type receiver 10 is shown in FIG. 14, which contains a hollow cylindrical body 11', four horizontal partition boards 11$h$ and four vertical partition boards 11$v$. The horizontal partition boards 11$h$ and the vertical partition boards 11$v$ all have half-way through slits, by which they are engaged with each other to form a divided wall structure 11". The divided wall structure 11" is plugged into the hollow cylindrical body 11' to form modified tunnel-type receiver 10.

In FIG. 15 a modified tube-type receiver 10 is shown, which contains a hollow cylindrical body 11', two cylindrical tube holders 14, and a plurality of receiving tubes 12'. Two axial grooves 141 are formed on a surrounding surface of the cylindrical tube holder 14, and two axial protrusions 111 corresponding to the axial grooves 141 are formed on an inner wall of the enlarged opening of the end of the hollow cylindrical body 11'. The two cylindrical tube holders 14 are mounted in the two ends of the hollow cylindrical body 11' with the axial grooves 141 being engaged with the axial protrusions 111, thereby the openings 15 of the two cylindrical tube holders 14 are aligned with one another, and then the receiving tubes 12' are received in the openings 15 of the two cylindrical tube holders 14 respectively. Each of the two ends of the hollow cylindrical body 11' has an enlarged opening having a diameter equal to an outer diameter of said cylindrical tube holder 14, wherein a regular opening is between the two ends of the hollow cylindrical body 11', and a vertical wall is at the interface of the enlarged opening and the regular opening, which is able to stop an insertion of the cylindrical tube holder 14 into the regular opening of the hollow cylindrical body 11'. The exit end 21 of the container 20 has a thinner wall portion (an enlarged opening) so that a proximal end 19 of the modified tube-type receiver 10 can be plugged into this thinner wall portion of the exit end 21 of the container 20, and so that the exit end 21 of the container 20 is in fluid communication with the plurality of receiving tubes 12' mounted in the openings 15 of the two cylindrical tube holders 14. A perforated cap 92 is mounted to a distal end of the receiver 10 to fasten an air-penetrable film 93 between the perforated cap 92 and the receiver 10 to avoid air accumulation in the receiving tubes 12' and to avoid the cement paste leaking from the receiver 10, when the cement paste 80 in the container 20 is pushed by the piston 70 to simultaneously flow into each receiving tube 12'.

Figure 16:
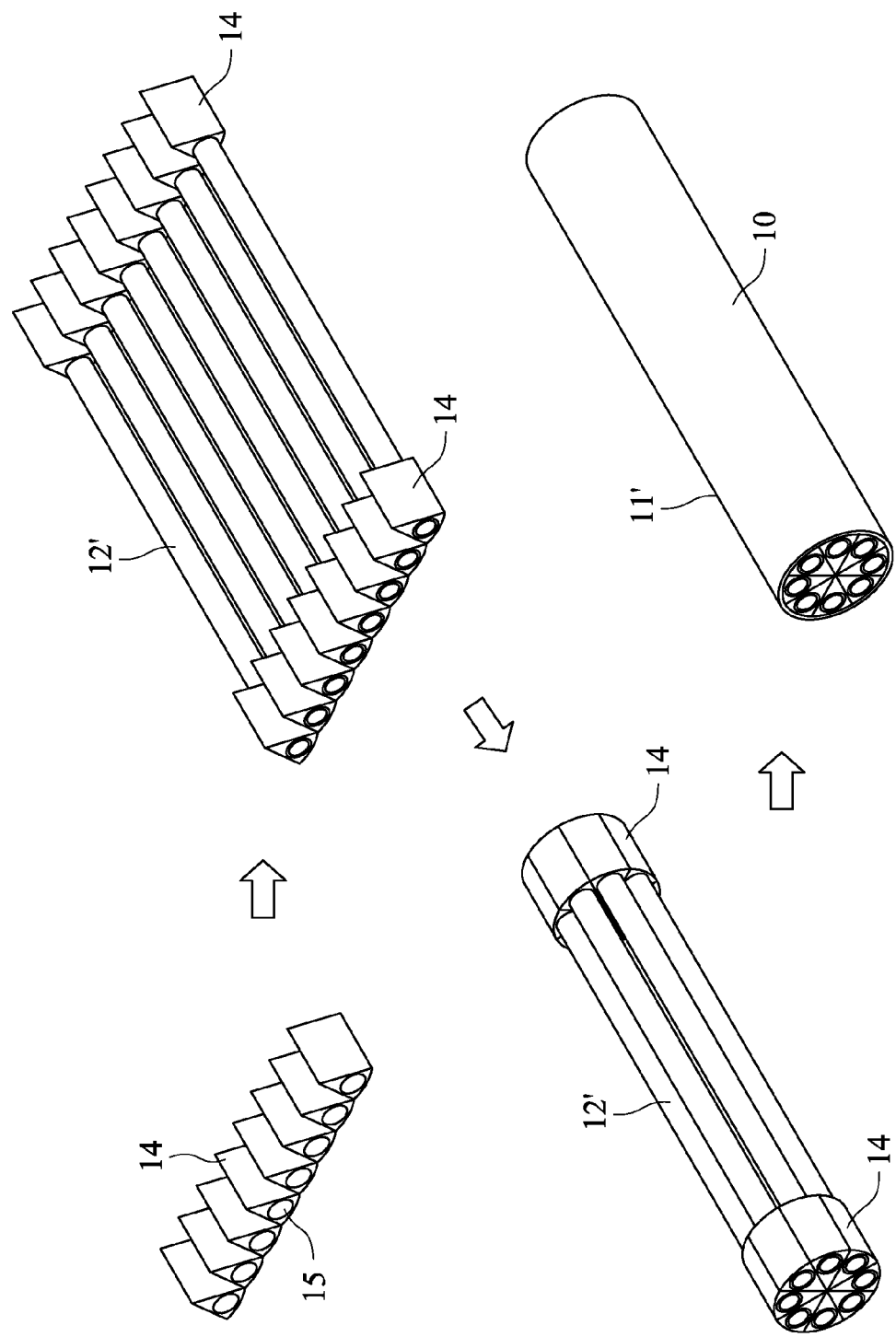
FIG. 16 shows a modified tube-type receiver for cement paste according to one embodiment of the present invention.

FIG. 16 shows another modified tube-type receiver 10, wherein eight receiving tubes 12' are received in the openings 15 of two rolls of ⅛-sector-divided cylindrical tube holders 14, which can then be rolled up and plugged into a hollow cylindrical body 11' to form the tube-type receiver 10.

Figure 17:
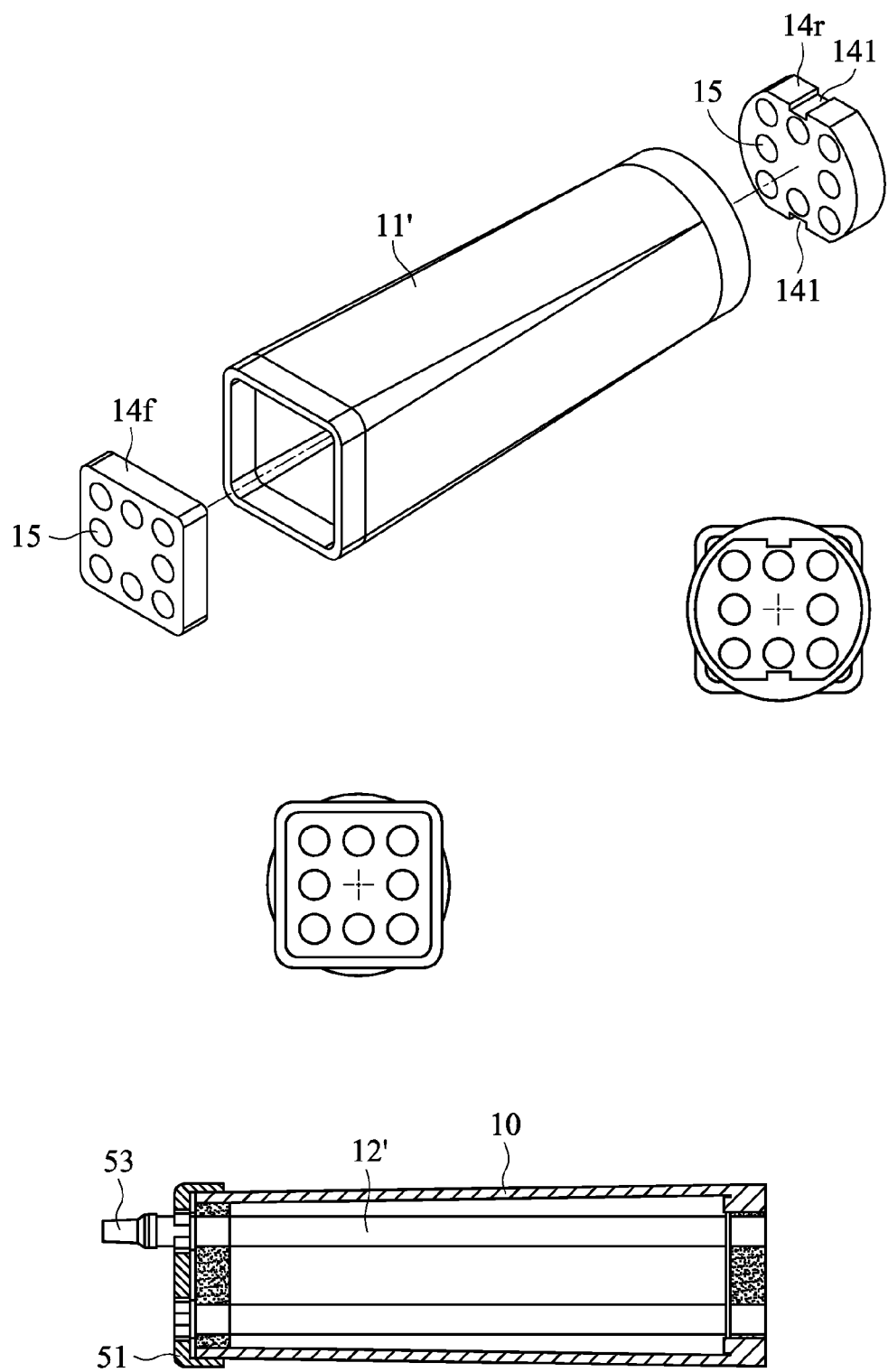
FIG. 17 shows a modified tube-type receiver for cement paste according to one embodiment of the present invention, which has a circular rear end and a square front end.
Figure 18:
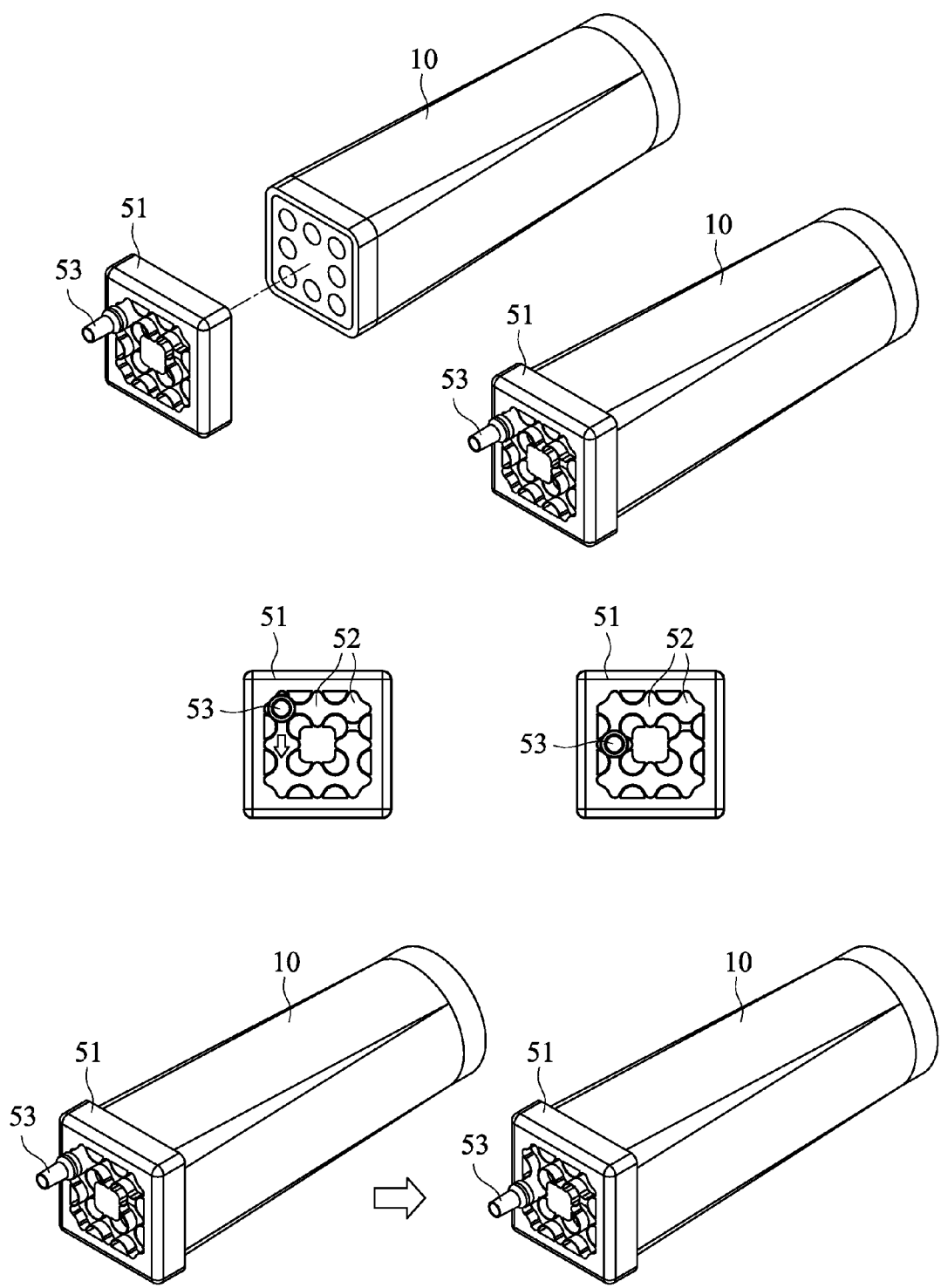
FIG. 18 shows the modified tube-type receiver in FIG. 17 together with an outlet adapter 51 capped onto the square front end thereof.

The receiver of the present invention is not necessarily cylindrical. As shown in FIGS. 17 and 18, the receiver 10 has a hollow body 11' which has a circular rear end and a square front end, a rear tube holder 14r with two axial grooves 141 plugged into the circular rear end, and a front tube holder 14f plugged into the square front end. The rear tube holder 14r and the front tube holder 14f both have eight openings 15 which are identical and aligned with one another, so that eight receiving tubes 12' can be received in the openings 15 to form a tube-type receiver 10. This tube-type receiver 10 has a circular rear end which is able to be connected to a cement paste container for filling the cement paste into the receiving tubes 12' as in the other embodiments of the present invention described above. An outlet adapter 51 is capped onto the square front end of the receiver 10 to facilitate the delivery of cement pastes filled in the eight receiving tubes 12'. The outlet adapter 51 is formed with a track defining eight stops 52 corresponding to eight receiving tubes 12' received in the eight openings 15 of the square front tube holder 14f, and a cement outlet 53 can be pushed to slide into and out from the eight stops 52 in the track one after another, whereby the cement paste filled in the receiving tubes 12' can be alternatively pushed out by a plunger into a surgical tube or a connecting tube via the cement outlet 53.

An outlet adapter 51 with a ratchet mechanism for delivering the cement paste in the receiver 10 is shown in FIG. 19. The outlet adapter 51 has a rotating seat 54, and the receiver 10 is rotatably received therein by the conventional spindle/round hole structure. The receiver 10 is provided with ratchet teeth 55 on its surface corresponding to the parallel tunnels 12 or receiving tubes 12' of the receiver 10, and the rotating seat 54 is provided with two detents 56 on its inner wall to engage with the ratchet teeth 55, so that the receiver 10 is only able to be rotated in one direction (counterclockwise). The rotating base 54 is provided with two axial holes which are in alignment with a parallel tunnel 12 or a receiving tube 12' of the receiver 10 when the detents 56 contact vertical walls of two of the ratchet teeth 55, and the rotating base 54 is further provided with a cement outlet 53 on one of the two axial holes, so that a plunger inserting into the other axial hole can push the cement paste filled in the parallel tunnel 12 or the receiving tubes 12' into a surgical tube or a connecting tube via the cement outlet 53. Accordingly, the cement paste in all the parallel tunnels 12 or receiving tubes 12' of the receiver 10 can be delivered one-by-one by ratcheting the receiver 10 in the rotating base 54.

Figure 20:
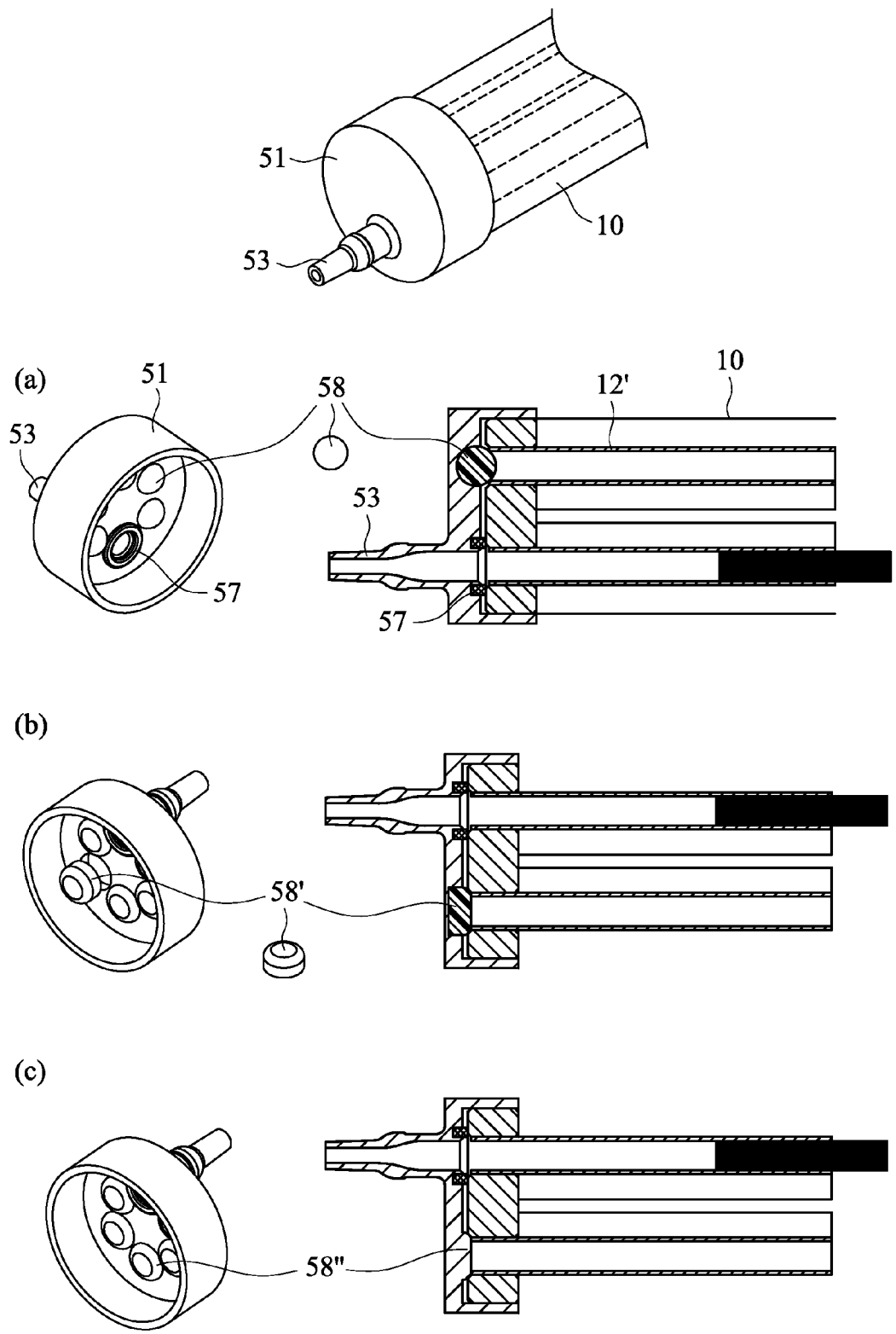
FIG. 20 shows a receiver for cement paste rotatably capped with an outlet adaptor having a sealing and blocking mechanism according to one embodiment of the present invention, wherein (a) to (c) show different embodiments of the sealing and blocking mechanism.

An outlet adaptor 51 with sealing and blocking mechanism for delivering the cement paste in the receiver 10 is shown in FIG. 20. The outlet adaptor 51 is formed with a cement outlet 53 at one side thereof and is rotatably connected to one end of the receiver 10 at another side thereof. The outlet adaptor 51 at the another side thereof is further provided with an O-ring 57 surrounding an opening of the cement outlet 53, a plurality of recesses, and a plurality of balls 58 received in the plurality of recesses, as shown in (a) In FIG. 20. The O-ring 57 assures that the cement outlet 53 and one of the receiving tubes 12' is in leak-tightly fluid communication with each other, while the balls 58 leak-tightly block the remaining receiving tube 12' of the receiver 10. Another similar outlet adaptor 51 is shown in (b) in FIG. 20, wherein the balls 58 in FIG. 20(*a*) are replaced with elastomer plugs 58'. Still another similar outlet adaptor 51 is shown in (c) in FIG. 20, wherein the recesses and the balls 58 in FIG. 20(*a*) are replaced with chamfered cylindrical plugs 58" integrally formed with the outlet adaptor. The outlet adaptors 51 shown in (a) to (c) in FIG. 20 can avoid the cement paste filled in the receiving tubes 12' from leaking when it is delivered from the receiving tubes 12' to a surgical tube or a connecting tube via the cement outlet 53 alternately.

Figure 21:
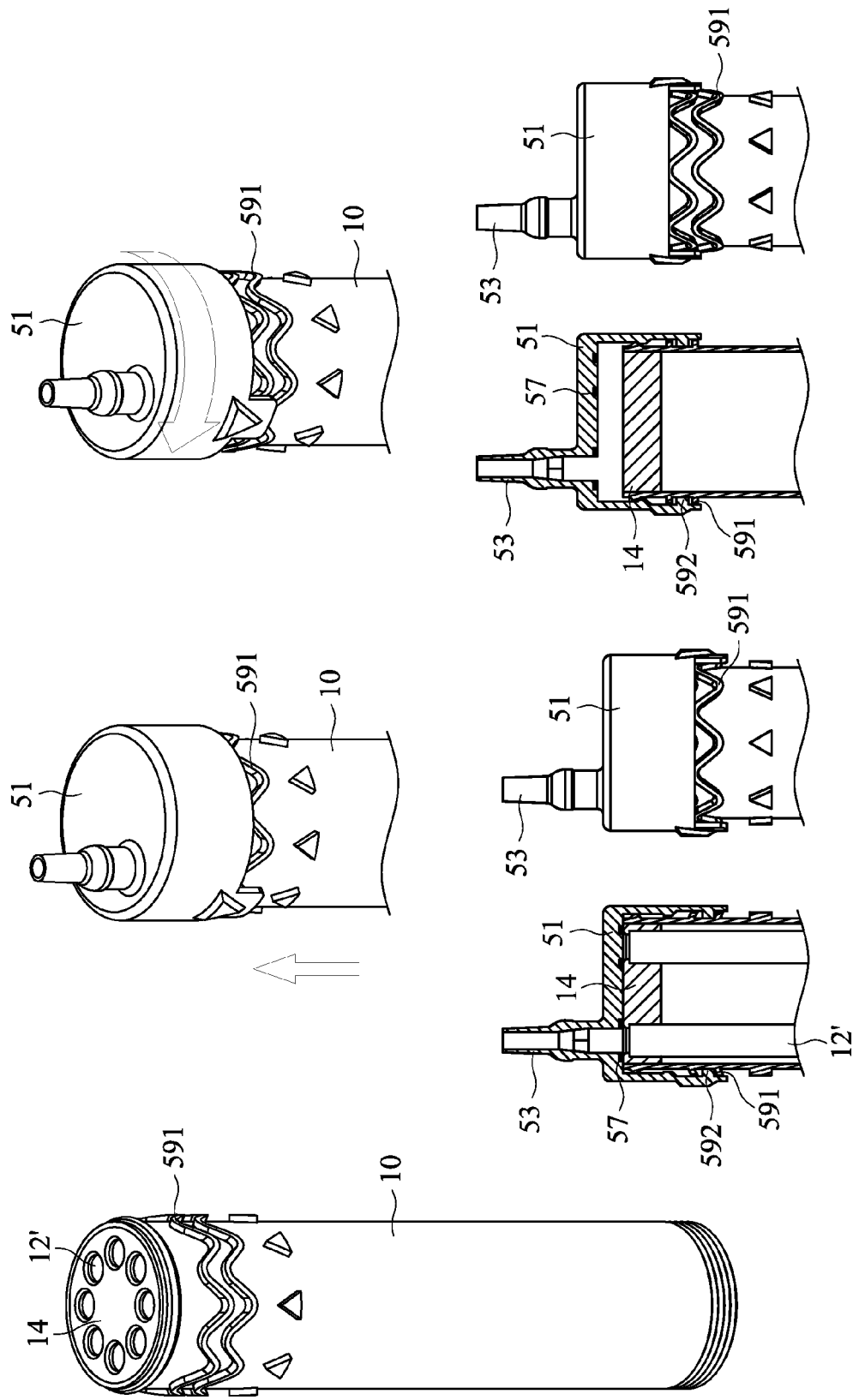
FIG. 21 shows a receiver for cement paste rotatably capped with an outlet adaptor, wherein a wave-like tack is formed around the surface of the receiver and a pair of sliding guides are formed oppositely on an inner wall of the outlet adaptor, whereby the outlet adaptor can move up and down when the outlet adaptor is turned.

A wave-like tack 591 can be formed around the surface of the receiver 10 as shown in FIG. 21. A pair of sliding guides 592 are formed oppositely on an inner wall of the outlet adaptor 51, which are received in the wave-like tack 591, so that the outlet adaptor 51 can move up and down when the outlet adaptor 51 is turned. The outlet adaptor 51 is formed with a cement outlet 53 at the outer side thereof, and at the opposite side thereof is further provided with O-rings 57 corresponding the receiving tubes 12 of the receiver 10, wherein one of the O-rings 57 surrounds an opening of the cement outlet 53. By the engagement of the sliding guides 592 and the wave-like tract 591, the O-rings 57 will be pressed by the tube holder 14 of the receiver 10, when the outlet adaptor 51 is turned to move down on the receiver 10; and the O-rings 57 will move frictionlessly, when the outlet adaptor 51 is turned to move up on the receiver 10. As a result, the cement paste filled in the receiving tubes 12' can be transported alternately into a surgical tube or connecting tube via the cement outlet 53 without leaking.

Although the present invention has been described with reference to specific details of certain embodiments thereof, it is not intended that such details should be regarded as limitations upon the scope of the present invention. Many modifications and variations are possible in light of the above disclosure.

The invention claimed is:

1. A filling apparatus comprising a plurality of parallel tunnels formed in a longitudinal body and in a longitudinal direction of said body; and a filler reservoir having an exit end adapted to be in fluid communication with said plurality of parallel tunnels, wherein a cross-sectional area of said exit end is less than 5 times of a total cross-sectional area of said plurality of parallel tunnels, so that a filler contained in said reservoir is able to be driven to flow non-circularly toward said exit end and into said plurality of tunnels simultaneously via said exit end, wherein said tunnels have an inner diameter of 1 mm to about 10 mm;

further comprising a plurality or receiving tubes wherein said longitudinal body is a hollow longitudinal body and said plurality of receiving tubes are separate elements and adapted to be releasably received in said hollow longitudinal body such that said plurality of parallel tunnels are formed in said plurality of receiving tubes;

further comprising two tube holders wherein each of the two tube holders comprises a multi-tubular structure with a plurality of openings, and the two tube holders are both adapted to be releasably connected to two ends of the hollow longitudinal body with said plurality of openings of the two tube holders being aligned with one another, such that said plurality of receiving tubes are mounted in said plurality of openings of the two tube holders respectively;

wherein the hollow longitudinal body is a hollow cylindrical body, and each of the two tube holders is a cylindrical tube holder, wherein each of the two ends of the hollow cylindrical body comprises an enlarged opening having a diameter equal to an outer diameter of said cylindrical tube holder; and the hollow cylindrical body comprises a narrower opening between the two ends of the hollow cylindrical body; and the hollow cylindrical body comprises a vertical wall at the interface of the enlarged opening and the narrower opening, which is able to stop an insertion of the cylindrical tube holder into the narrower opening of the hollow cylindrical body, wherein an alignment mechanism is provided on each of the two ends of the hollow cylindrical body and on the cylindrical tube holder such that said plurality of receiving tubes are mounted in said plurality of openings of the two tube holders respectively and in parallel when the two cylindrical tube holders are connected to said two ends of the hollow cylindrical body.

2. The apparatus of claim 1, wherein said tunnels have a length of about 10 mm to 300 mm.

3. The apparatus of claim 1, wherein the cross-sectional area of said exit end is less than about 3 times of a total cross-sectional area of said plurality of parallel tunnels.

4. The apparatus of claim 1, wherein the cross-sectional area of said exit end is about 1.5 to about 1.1 times of a total cross-sectional area of said plurality of parallel tunnels.

5. The apparatus of claim 1, wherein the alignment mechanism comprises an axial groove formed on a surrounding surface of the cylindrical tube holder, and an axial protrusion corresponding to the axial groove formed on an inner wall of the enlarged opening of the end of the hollow cylindrical body, or vice versa.

6. The apparatus of claim 1, wherein said exit end of said reservoir has a thinner wall portion having an inner diameter equal to an outer diameter of said longitudinal body, so that one end of said longitudinal body can be plugged into this thinner wall portion of the exit end of said reservoir.

7. The apparatus of claim 1 further comprising a driver for driving the filler contained in said reservoir into said plurality of parallel tunnels via said exit end.

8. The apparatus of claim 7 further comprising an air-penetrable film being provided to cover one end of said longitudinal body, so that air in said plurality of parallel tunnels is pushed out by said filler and said filler is retained in said plurality of parallel tunnels, when said filler contained in said reservoir is driven into said plurality of parallel tunnels by said driver.

9. The apparatus of claim 7, wherein said reservoir comprises a cylindrical container for receiving said filler, and said driver is a dispensing plunger slidably received in said cylindrical container, so that the filler contained in said cylindrical container is able to be pushed by the plunger into said plurality of parallel tunnels via said exit end.

10. The apparatus of claim 1, wherein the filler reservoir has a volume for containing a filler close to or greater than a total volume of said plurality of tunnels, so that said plurality of tunnels are able to be filled with the filler in the filler reservoir.

11. The apparatus of claim 1, wherein the longitudinal body is non-flexible.

* * * * *